US 6,652,458 B2

(12) United States Patent
Blazey et al.

(10) Patent No.: US 6,652,458 B2
(45) Date of Patent: Nov. 25, 2003

(54) ADHD DETECTION BY EYE SACCADES

(75) Inventors: Richard N. Blazey, Penfield, NY (US); David L. Patton, Webster, NY (US); Peter A. Parks, Topeka, KS (US)

(73) Assignee: The McLean Hospital Corporation, Belmont, MA (US)

( * ) Notice: Subject to any disclaimer, the term of this patent is extended or adjusted under 35 U.S.C. 154(b) by 28 days.

(21) Appl. No.: 09/866,183

(22) Filed: May 25, 2001

(65) Prior Publication Data

US 2003/0028081 A1 Feb. 6, 2003

Related U.S. Application Data

(63) Continuation-in-part of application No. 09/597,610, filed on Jun. 20, 2000, now Pat. No. 6,394,963.

(51) Int. Cl.[7] .................................................. A61B 5/00
(52) U.S. Cl. .................... 600/300; 600/595; 351/210
(58) Field of Search ................... 600/300, 301, 600/558, 595; 128/903, 904; 351/209, 210

(56) References Cited

U.S. PATENT DOCUMENTS

| | | | |
|---|---|---|---|
| 4,456,347 A | | 6/1984 | Stahly |
| 4,889,422 A | * | 12/1989 | Pavlidis ..................... 351/210 |
| 5,377,100 A | | 12/1994 | Pope et al. |
| 5,913,310 A | | 6/1999 | Brown |
| 5,918,603 A | | 7/1999 | Brown |
| 5,940,801 A | | 8/1999 | Brown |
| 6,053,739 A | | 4/2000 | Stewart et al. |
| 6,097,980 A | | 8/2000 | Monastra et al. |
| 6,117,075 A | | 9/2000 | Barnea |
| 6,231,187 B1 | * | 5/2001 | Munoz et al. ............. 351/209 |

OTHER PUBLICATIONS

Munoz, D.P. et al, Control of Purposive Saccadic Eye Movements and Visual Fixation in Children with Attention–Deficit Hyperactivity Disorder, 1999, Plenum Publishing, Current Oculomotor Research: Physiological and Psychological Aspects pp. 1–9.*

Munoz, D.P. et al, Attentional and Psychiatric Influences on Gaze, 1997, North American Neuro–ophthalmology Society, pp. 237–240.*

Disclosure on the Development of EEG Diagnostics and Biofeedback for Attention–Deficit/Hyperactivity Disorders, Joel F. Lubar, Biofeedback and Self–Regulation, vol. 6, No. 3, 191.

Functional Deficits in Basal Ganglia of Children with Attention–Deficit/Hyperactivity Disorder Shown with Functional Magnetic Resonance Imaging Relaxometry, Teichler et al., Nature Magazine, Apr. 2000, vol. 6, No. 4, pp 470–473.

Human Factors and Cognitive/Perceptual Information Processing, A virtuality Reality Environment for the Assessment of Attention Deficit Disorders in Children, Rizzo et al., Human Factors and Cognitive/Perceptual information Processing, University of Southern California, Jul. 1999.

Clinical Practice Guideline: Diagnosis and Evaluation of the Child with Attention–Deficit/Hyperactivity Disorder, Homer et al., American Academy of Pediatrics.

* cited by examiner

*Primary Examiner*—Eric F. Winakur
*Assistant Examiner*—David J. McCrosky
(74) *Attorney, Agent, or Firm*—Clark & Elbing, LLP; Paul T. Clark

(57) ABSTRACT

A method of determining whether an individual has Attention Deficit Hyperactivity Disorder comprising: sampling the eye movement of a human subject during a predetermined time interval when the subject is in an inactive state to provide sampled eye movement data; and analyzing the sampled eye movement data for a pre-selected parameter, to determine whether said pre-selected parameter has a value indicative of ADHD.

30 Claims, 3 Drawing Sheets

ADHD DETECTION BY EYE SACCADES

CROSS REFERENCE TO RELATED APPLICATIONS

This Continuation-in-Part patent application claims the benefit under 35 USC §120 of the earlier filing date of U.S. patent application Ser. No. 09/597,610, filed Jun. 20, 2000, now U.S. Pat. No. 6,394,963.

FIELD OF THE INVENTION

This invention relates in general to a technique for diagnosing Attention Deficit Hyperactivity Disorder (ADHD) using a biological metric such as eye saccades.

BACKGROUND OF THE INVENTION

ADHD is the most common neurobehavioral disorder of childhood as well as among the most prevalent health conditions affecting school-aged children. Between 4% and 12% of school age children (several millions) are affected. $3 billion is spent annually on behalf of students with ADHD. Moreover, in the general population, 9.2% of males and 2.9% of females are found to have behavior consistent with ADHD. Upwards of 10 million adults may be affected.

ADHD is a difficult disorder to diagnose. The core symptoms of ADHD in children include inattention, hyperactivity, and impulsivity ADHD children may experience significant functional problems, such as school difficulties, academic underachievement, poor relationships with family and peers, and low self-esteem. Adults with ADHD often have a history of losing jobs, impulsive actions, substance abuse, and broken marriages. ADHD often goes undiagnosed if not caught at an early age and affects many adults who may not be aware of the condition. ADHD has many look-alike causes (family situations, motivations) and co-morbid conditions (depression, anxiety, learning disabilities).

Diagnosis of ADHD involves a process of elimination using written and verbal tests. However, there is no one objective, independent valid test for ADHD. Various objective techniques have been proposed but have not yet attained acceptance. These include:

1. The eye problem called convergence insufficiency was found to be three times more common in children with ADHD than in other children by David Granet at the University of California, San Diego.

2. Infrared tracking to measure difficult-to-detect movements of children during attention tests combined with functional MRI imaging of the brain were used by psychiatrists at McLean Hospital in Belmont, Mass. to diagnose ADHD in a small group of children (*Nature Medicine*, Vol. 6, No. 4, April 2000, Pages 470–473).

3. Techniques based on EEG biofeedback for the diagnoses and treatment of ADHD are described by Lubar (*Biofeedback and Self-Regulation*, Vol. 16, No. 3, 1991, Pages 201–225).

4. U.S. Pat. No. 6,097,980, issued Aug. 1, 2000, inventor Monastra et al, discloses a quantitative electroencephalographic process assessing ADHD.

5. U.S. Pat. No. 5,913,310, issued Jun. 22, 1999, inventor Brown, discloses a video game for the diagnosis and treatment of ADHD.

6. U.S. Pat. No. 5,918,603, issued Jul. 6, 1999, inventor Brown, discloses a video game for the diagnosis and treatment of ADHD.

7. U.S. Pat. No. 5,940,801, issued Aug. 17, 1999, inventor Brown, discloses a microprocessor such as a video game for the diagnosis and treatment of ADHD.

8. U.S. Pat. No. 5,377,100, issued Dec. 27, 1994, inventors Pope et al., discloses a method of using a video game coupled with brain wave detection to treat patients with ADHD.

9. Dr. Albert Rizzo of the Integrated Media Systems Center of the University of Southern California has used Virtual Reality techniques for the detection and treatment of ADHD.

10. U.S. Pat. No. 6,053,739, inventors Stewart et al., discloses a method of using a visual display, colored visual word targets and colored visual response targets to administer an attention performance test.

11. U.S. Pat. No. 5,377,100, issued Dec. 27, 1994, inventors Patton et al., discloses a system and of managing the psychological state of an individual using images.

12. U.S. Pat. No. 6,117,075 Barnea discloses a method of measuring the depth of anesthesia by detecting the suppression of peripheral temperature variability.

As discussed above, the primary method for diagnosing ADHD is the use of a bank of written and verbal assessment instruments designed to assess criteria established by American Medical Association (AMA) as described in the Diagnostic and Statistics manual—IV (DSM-IV) and administered by the school psychologist or other licensed practitioner. Most recently the American Academy of Pediatrics issued guidelines, which are widely followed (Clinical Practice Guidelines: Diagnosis of a child with Attention Deficit Hyperactivity Disorder; Pediatrics V5 #105 5 May 2000). In some cases those individuals who meet DSM-IV criteria for ADHD diagnosis are prescribed a drug such as RITALIN (methylphenidate). Behavioral observations of the patient while on RITALIN are conducted to assess the impact of prescribed medication.

There are several clinical biofeedback and physiology monitoring systems (e.g. Multi Trace, Bio Integrator). These systems are used by professional clinicians. A clinician monitors patient's physiologic changes and accordingly uses different protocols.

U.S. patent application Ser. No. 09/597,610 describes an apparatus and method of determining whether an individual has Attention Deficit Hyperactivity Disorder by analyzing physiologic reactivity patterns (peripheral skin temperature) when the subject is asked to sit quietly in a low stimulus environment for a short period of time.

SUMMARY OF THE INVENTION

According to the present invention, there is provided a solution to the problems and fulfillment of the needs discussed above.

According to a feature of the present invention, there is provided a method of determining whether an individual has Attention Deficit Hyperactivity Disorder comprising: sampling the eye movement of a human subject during a predetermined time interval when the subject is in an inactive state to provide sampled eye movement data; and analyzing the sampled eye movement data for a pre-selected parameter, to determine whether said pre-selected parameter has a value indicative of ADHD.

ADVANTAGEOUS EFFECT OF THE INVENTION

The invention has the following advantages.

1. A technique for diagnosing ADHD is provided which is simple, inexpensive and reliable.

DETAILED DESCRIPTION OF THE INVENTION

According to the present invention, it has been found that a signature of ADHD is the angular acceleration of the eyeball. In a set of experiments, the angular acceleration of the eyeball was measured during the same baseline period when the subject was asked to sit quietly.

Figure 1:
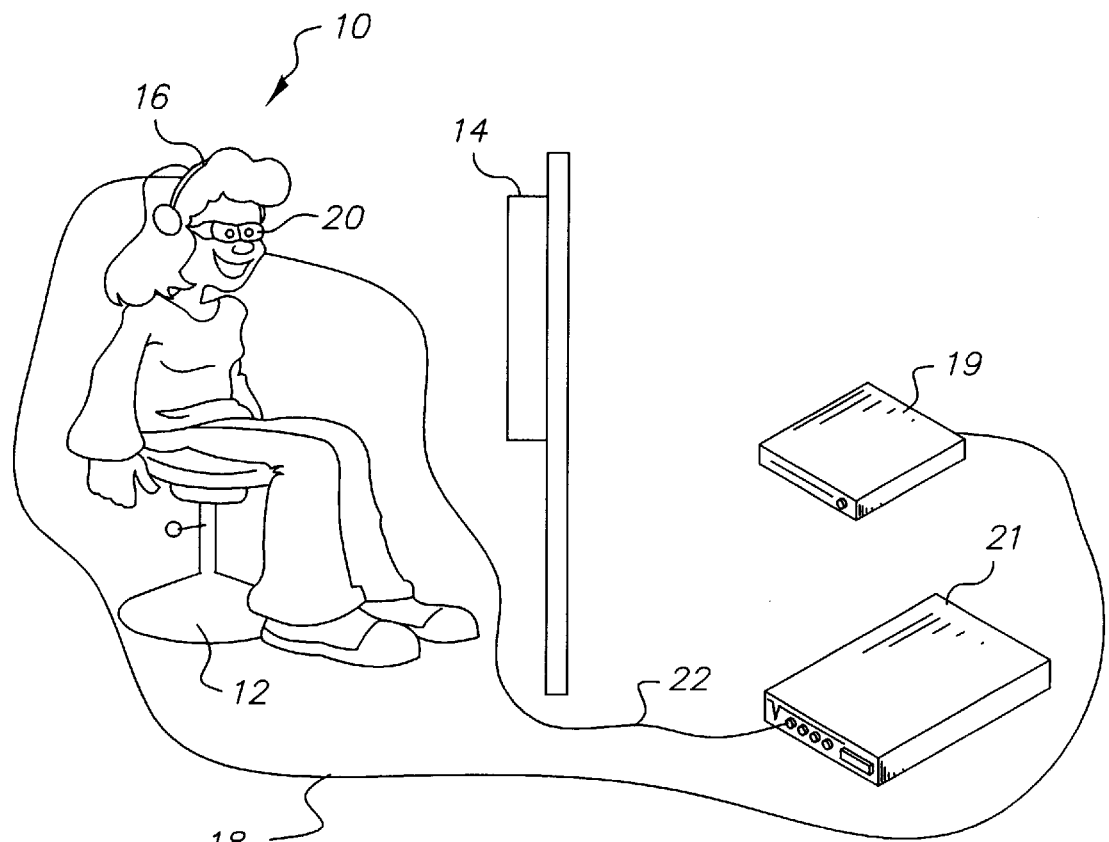
FIG. 1 is a diagrammatic view of the apparatus of the present invention.

As shown in FIG. 1, a subject 10 is sitting on a chair 12 viewing a blank screen 14. The subject is at rest in an inactive state. The subject 10 is shown wearing a set of earphones 16 connected via a wire 18 to a sound generating device 19. The earphones 16 can be used to block out ambient noise or produce a white noise intended to reduce or eliminate the audio stimulus from the environment during the test. The method described in this embodiment of the present invention places the subject in sensory deprived surroundings. The subject 10 wears a pair of glasses 20. The glasses 20 are connected to module 21 via a wire 22. The glasses 20 are equipped with a device 30 shown in FIG. 2 used for measuring the angular acceleration of the eyeball as described in U.S. Pat. No. 4,456,347, issued Jun. 26, 1984, inventor F. A. Stahly. The method of measuring the angular acceleration of the eyeball of the subject 10 is described in FIG. 2.

Figure 2:
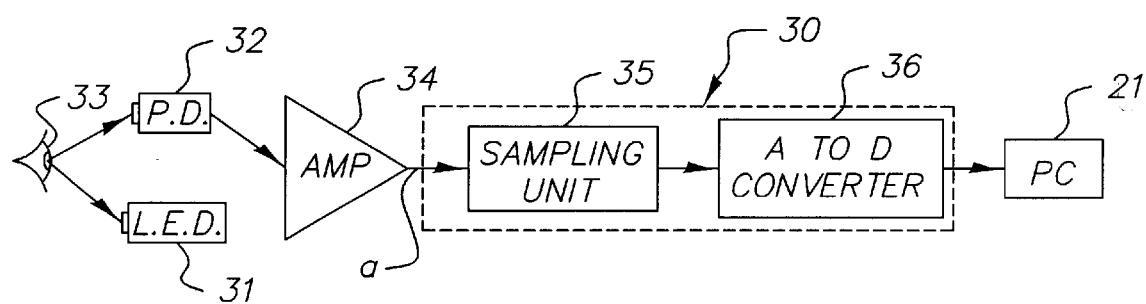
FIG. 2 is a block diagram of the apparatus.

Referring now to FIG. 2, as described in U.S. Pat. No. 4,456,347, three light transducing elements comprising an infrared radiator in the form of a light-emitting diode (LED) 31 and a pair of infrared-sensitive photo diodes 32, are supported in a mounting unit such as glasses 20 as shown in (FIG. 1). Appropriate wiring to a small electronic circuit (not shown) connects the light transducing elements 31 and 32. The elements are adjusted so that radiant energy from LED 31 is directed to the surface of the eye 33 (or the closed eyelid) of the wearer so that reflections of that radiation are received by photodiodes 32. Any slight movement of the individual's eye 33 causes a change in the reflectivity of the particular area of the individual's eye 33 or closed eyelid on which the radiant energy is impinging. For instance, any resulting alteration of the patterns of tiny blood vessels in the sclera, or any minute modifications in the contours of an eyelid, will result in respective changes in such reflectively. Any such minute change in reflectivity is accompanied by a corresponding change in the output signals of photodiodes 32, which vary in amplitude in accordance with the size and duration of the saccadic movement.

The output of the photodiodes 32 is fed to differential amplifier 34. The device 30 receives the differential signal from the amplifier at point "a". The signal is collected and then sampled at 1024 s/sec by sampling unit 35, converted to a digital signal by A/D converter 36 and stored in a data file located in storage module 21 as shown in FIG. 1. Module 21 can be a digital computer or other type of logic and control unit. The equipment shown within the dotted border 30 can be part of a digital data acquisition system such as the DSP-330 made by the J+J Engineering Company. Model 21 can be located at the test site or be remote from it. Thus, signals can be transmitted over a wireless channel to a remote site for analysis. The signals can also be transmitted over any telecommunication channel, telephone, cable, satellite, Internet, etc., for analysis at a remote site.

Figure 3:
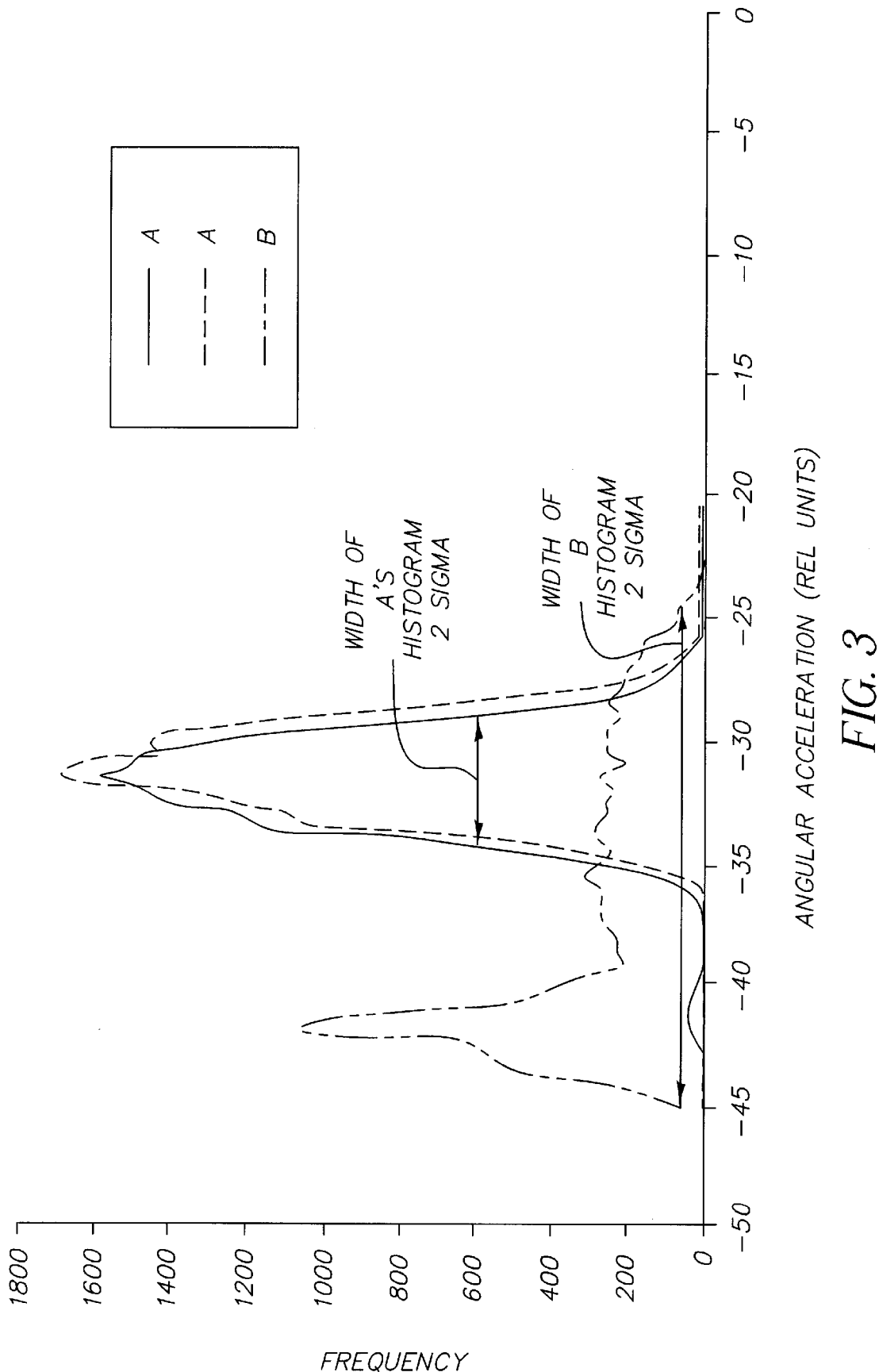
FIGS. 3 and 4 are graphical views useful in explaining the present invention.
Figure 4:
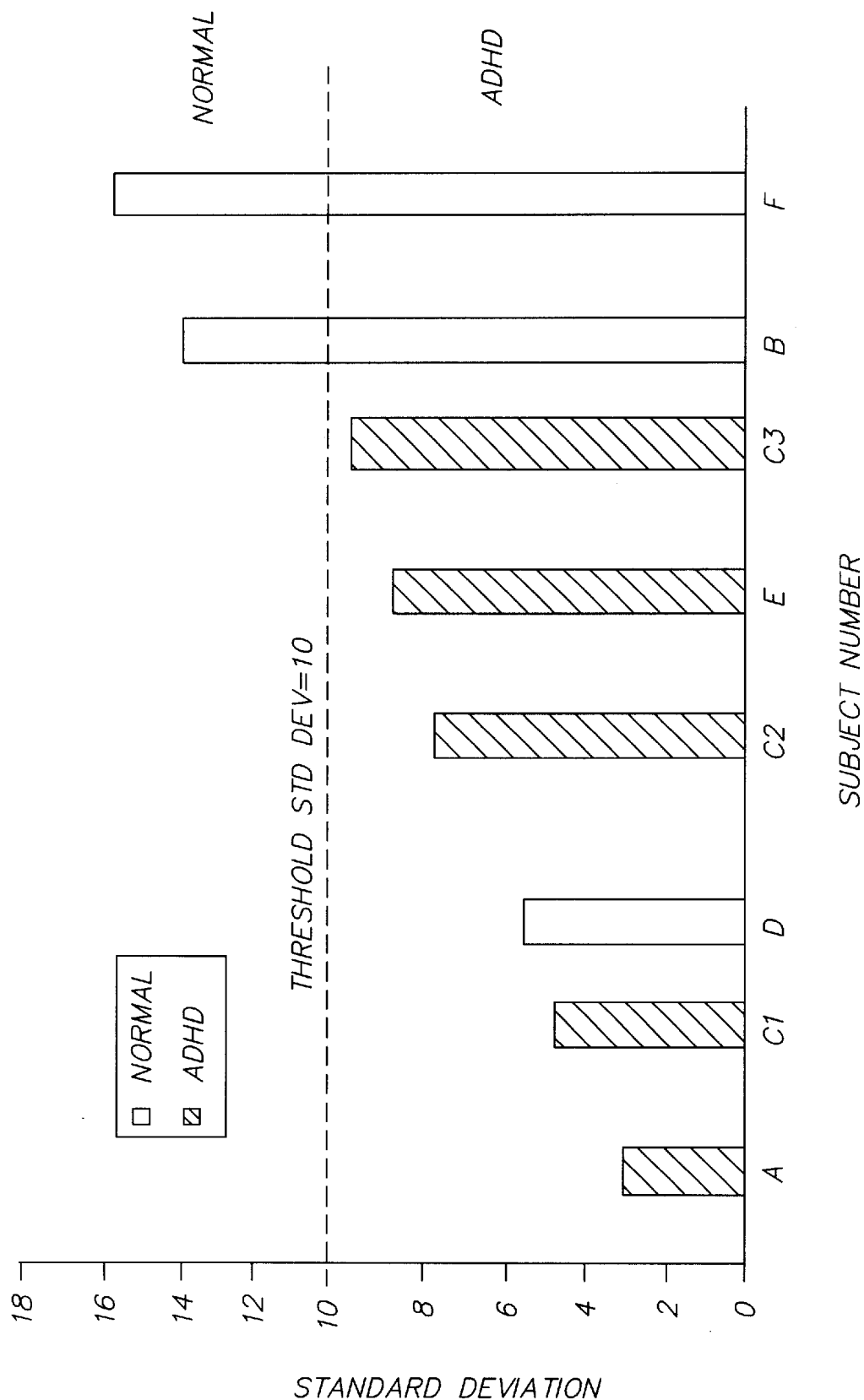

Using the device described in FIG. 2, the pupillary angle of a human subject is sampled during a predetermined time interval when the subject is in an inactive state. The angular acceleration of the eye at equally spaced intervals is measured while the subject 10 stares at the blank screen 14 during the test period. The test period can be approximately 10 minutes in length. The measurement data of the angular acceleration of the eye is plotted in the form of a histogram as shown in FIGS. 3 and 4. The width of the histogram is measured at a chosen fraction of the maximum value and compared to a threshold value. Widths below the threshold value provide a diagnosis of ADHD and widths above the threshold value constitute a diagnosis of normal.

Referring to FIG. 3, histograms show the eye acceleration data for 2 subjects A and B. Subject A is diagnosed with having ADHD. Subject B is diagnosed with not having ADHD. The narrower width of Subject A's histogram as compared to Subject B's histogram indicates a smaller range of eye acceleration. The width of the histogram w is measured at the 2 σ points [w=2σ], where σ is the standard deviation as defined by the following equation $$\sigma(\tau) = \frac{1}{n} \sum_{i=0}^{i=n} [a_i - \mu(a)]^2$$

Where a is the angular acceleration of the eye in relative units and n is the number of samples and τ is the time at the start of a temporal window containing n samples.

Referring now to FIG. 4, the standard deviations of the histograms of the eye saccades measured for 7 (subjects including subjects A & B shown in FIG. 3) are shown. These data were obtained by averaging the histogram widths measured from 5 windows spaced equally in time. With the exception of subject D, all subjects with ADHD diagnosis have narrower histograms then the normal subjects. The data demonstrates that the range of eye motion can be used as a diagnostic method for ADHD. When the width of a histogram (as shown on the ordinate of FIG. 4) is less than a threshold value Θ the subject is diagnosed as having ADHD, when the width is greater than Θ (shown by a dotted line on FIG. 4) the subject is diagnosed as normal. Setting a value of 10 for Θ would give only one false positive result out of 8 test runs shown on FIG. 4, an accuracy of 87.5%.

The invention has been described in detail with particular reference to certain preferred embodiments thereof but it will be understood that variations and modifications can be effected within the spirit and scope of the invention.

| PARTS LIST | |
|---|---|
| 10 | human subject |
| 12 | chair |
| 14 | blank screen |
| 16 | earphones |
| 18 | wire |
| 19 | sound generating device |
| 20 | glasses |
| 21 | module |
| 22 | wire |
| 30 | device |
| 31 | light emitting diode (LED) |
| 32 | photodiodes |
| 33 | eye |
| 34 | amplifier |
| 35 | sampling unit |
| 36 | A/D converter |

What is claimed is:

1. A method of determining whether an individual has Attention Deficit Hyperactivity Disorder comprising:

sampling the eye movement of a human subject during a predetermined time interval when the subject is in an inactive state with no visual stimulus to provide sampled eye movement data; and analyzing the sampled eye movement data for a pre-selected parameter, to determine whether said pre-selected parameter has a value indicative of ADHD.

2. The method of claim 1 wherein said sampling includes sampling the pupillary angle of an eye of said human subject during a predetermined time interval when the subject is in an inactive state; and wherein said analyzing includes measuring the angular acceleration of said eye from said pupillary angle samples at equally spaced intervals during a predetermined time interval.

3. The method of claim 2 wherein said analyzing includes plotting said angular acceleration measurements in the form of a histogram;

measuring the width of said histogram at a chosen fraction of the maximum value; and comparing the measured width to a threshold value with widths below said threshold value indicative of a diagnosis of ADHD and widths above the threshold value indicative of normal.

4. The method of claim 1 wherein said sampling includes irradiating an eye of said human subject with infrared radiation from a source and detecting reflections of said radiation from said eye with a radiation sensitive device.

5. The method of claim 4 wherein said source of infrared radiation and said radiation sensitive device are mounted on glasses worn by said human subject.

6. The method of claim 1 wherein said sampled eye movement data is transmitted to a remote site via a wired or wireless transmission channel, and wherein said analyzing is carried out at said remote site.

7. The method of claim 6 wherein said transmission channel includes one or more of transmission channels, telephone, cable, satellite, internet.

8. The method of claim 1 wherein during said predetermined time interval when said subject is in an inactive state, the subject wears an earphone to block out ambient noise or to receive white noise to reduce or eliminate audio stimulus from the ambient environment during said time interval.

9. A system for determining whether an individual has ADHD comprising;

a device for sampling the eye movement of a human subject during a predetermined time interval when the subject is in an inactive state with no visual stimulus to provide sampled eye movement data; and an analyzer for analyzing the sampled eye movement data for a pre-selected parameter to determine whether said pre-selected parameter has a value indicative of ADHD.

10. The system of claim 9 wherein said device for sampling samples the pupillary angle of an eye of said human subject during a predetermined time interval when said subject is in an inactive state; and wherein said analyzer measures the angular acceleration of said eye from said pupillary angle samples at equally spaced intervals during a predetermined time interval.

11. The system of claim 9 wherein said analyzer;

(a) plots the angular acceleration measurements in the form of a histogram;

(b) measures the width of said histogram at a chosen fraction of the maximum value; and (c) compares the measured width to a threshold value with widths below said threshold value indicative of a diagnosis of ADHD and widths above the threshold value indicative of normal.

12. The system of claim 9 wherein said sampling device includes a source of infrared radiation for irradiating an eye of said human subject with infrared radiation, and further includes an infrared radiation sensitive device for detecting reflections of said radiation from said eye.

13. The system of claim 12 wherein said source of infrared radiation and said infrared radiation sensitive device are mounted on glasses worn by said human subject.

14. The system of claim 9 including a transmitter for transmitting said sampled eye movement data to a remote site via a wired or wireless transmission channel and wherein said analyzer is located at said remote site.

15. The system of claim 14 wherein said transmission channel includes one or more of telephone, cable, satellite, Internet transmission channels.

16. A method of determining whether an individual has Attention Deficit Hyperactivity Disorder comprising:

sampling the eye movement of a human subject during a predetermined time interval when the subject is in sensory deprived surroundings to provide sampled eye movement data; and analyzing the sampled eye movement data for a pre-selected parameter, to determine whether said pre-selected parameter has a value indicative of ADHD.

17. The method of claim 16 wherein said sampling includes sampling the pupillary angle of an eye of said human subject during a predetermined time interval when the subject is in sensory deprived surroundings; and wherein said analyzing includes measuring the angular acceleration of said eye from said pupillary angle samples at equally spaced intervals during a predetermined time interval.

18. The method of claim 17 wherein said analyzing includes plotting said angular acceleration measurements in the form of a histogram;

measuring the width of said histogram at a chosen fraction of the maximum value; and comparing the measured width to a threshold value with widths below said threshold value indicative of a diagnosis of ADHD and widths above the threshold value indicative of normal.

19. The method of claim 16 wherein said sampling includes irradiating an eye of said human subject with infrared radiation from a source and detecting reflections of said radiation from said eye with a radiation sensitive device.

20. The method of claim 19 wherein said source of infrared radiation and said radiation sensitive device are mounted on glasses worn by said human subject.

21. The method of claim 16 wherein said sampled eye movement data is transmitted to a remote site via a wired or wireless transmission channel, and wherein said analyzing is carried out at said remote site.

22. The method of claim 21 wherein said transmission channel includes one or more of transmission channels, telephone, cable, satellite, internet.

23. The method of claim 16 wherein during said predetermined time interval when said subject is in an inactive state, the subject wears an earphone to block out ambient noise or to receive white noise to reduce or eliminate audio stimulus from the ambient environment during said time interval.

24. A system for determining whether an individual has ADHD comprising;
- a device for sampling the eye movement of a human subject during a predetermined time interval when the subject is in sensory deprived surroundings to provide sampled eye movement data; and
- an analyzer for analyzing the sampled eye movement data for a pre-selected parameter to determine whether said pre-selected parameter has a value indicative of ADHD.

25. The system of claim 24 wherein said device for sampling samples the pupillary angle of an eye of said human subject during a predetermined time interval when said subject is in sensory deprived surroundings; and
- wherein said analyzer measures the angular acceleration of said eye from said pupillary angle samples at equally spaced intervals during a predetermined time interval.

26. The system of claim 24 wherein said analyzer;
- (a) plots the angular acceleration measurements in the form of a histogram;
- (b) measures the width of said histogram at a chosen fraction of the maximum value; and
- (c) compares the measured width to a threshold value with widths below said threshold value indicative of a diagnosis of ADHD and widths above the threshold value indicative of normal.

27. The system of claim 24 wherein said sampling device includes a source of infrared radiation for irradiating an eye of said human subject with infrared radiation, and further includes an infrared radiation sensitive device for detecting reflections of said radiation from said eye.

28. The system of claim 27 wherein said source of infrared radiation and said infrared radiation sensitive device are mounted on glasses worn by said human subject.

29. The system of claim 24 including a transmitter for transmitting said sampled eye movement data to a remote site via a wired or wireless transmission channel and wherein said analyzer is located at said remote site.

30. The system of claim 29 wherein said transmission channel includes one or more of telephone, cable, satellite, Internet transmission channels.

* * * * *